(12) United States Patent
Salvati et al.

(10) Patent No.: US 8,084,447 B2
(45) Date of Patent: Dec. 27, 2011

(54) PHARMACEUTICAL COMPOSITION COMPRISING GABAPENTIN OR AN ANALOGUE THEREOF AND AN α-AMINOAMIDE AND ITS ANALGESIC USE

(75) Inventors: Patricia Salvati, Arese (IT); Orietta Veneroni, Milan (IT); Roberto Maj, Saronno (IT); Ruggero Fariello, Luino (IT); Luca Benatti, Cologno Monzese (IT)

(73) Assignee: Newron Pharmaceuticals S.p.A., Bresso (IT)

( * ) Notice: Subject to any disclaimer, the term of this patent is extended or adjusted under 35 U.S.C. 154(b) by 778 days.

(21) Appl. No.: 10/487,931

(22) PCT Filed: Aug. 9, 2002

(86) PCT No.: PCT/EP02/08910
§ 371 (c)(1),
(2), (4) Date: Jul. 26, 2004

(87) PCT Pub. No.: WO03/020273
PCT Pub. Date: Mar. 13, 2003

(65) Prior Publication Data
US 2004/0248978 A1 Dec. 9, 2004

(30) Foreign Application Priority Data
Sep. 3, 2001 (EP) .................. 01121069

(51) Int. Cl.
  *A01N 37/12* (2006.01)
  *A01N 37/46* (2006.01)
  *A61K 31/195* (2006.01)
(52) U.S. Cl. ........................ 514/183; 514/561
(58) Field of Classification Search .......... 514/183, 514/561
See application file for complete search history.

(56) References Cited

U.S. PATENT DOCUMENTS

| | | |
|---|---|---|
| 3,549,690 A | 12/1970 | Leigh et al. |
| 3,576,864 A | 4/1971 | Nagarajan |
| 3,658,967 A | 4/1972 | Leigh et al. |
| 4,024,175 A | 5/1977 | Satzinger et al. |
| 4,049,663 A | 9/1977 | Harper et al. |
| 4,087,544 A | 5/1978 | Satzinger et al. |
| 4,267,354 A | 5/1981 | Krapcho et al. |
| 4,311,853 A | 1/1982 | Cree et al. |
| 4,513,009 A | 4/1985 | Roques et al. |
| 4,602,017 A | 7/1986 | Sawyer et al. |
| 4,631,287 A | 12/1986 | Chakraborty et al. |
| 4,639,468 A | 1/1987 | Roncucci et al. |
| 4,725,608 A | 2/1988 | Nakaguchi et al. |
| 4,725,619 A | 2/1988 | Chakraborty et al. |
| 4,839,369 A | 6/1989 | Youssefyeh et al. |
| 4,894,476 A | 1/1990 | Butler et al. |
| 4,927,835 A | 5/1990 | Kise et al. |
| 4,927,836 A | 5/1990 | Holloway et al. |
| 5,025,035 A | 6/1991 | Wallace |
| 5,179,109 A | 1/1993 | Kamenka et al. |
| 5,236,957 A | 8/1993 | Dostert et al. |
| 5,256,669 A | 10/1993 | Askanazi et al. |
| 5,330,515 A | 7/1994 | Rutecki et al. |
| 5,391,577 A | 2/1995 | Dostert et al. |
| 5,446,066 A | 8/1995 | Varasi et al. |
| 5,449,692 A | 9/1995 | Varasi et al. |
| 5,475,007 A | 12/1995 | Cai et al. |
| 5,482,964 A | 1/1996 | Hays |
| 5,498,610 A | 3/1996 | Chenard |
| 5,502,079 A | 3/1996 | Dostert et al. |
| 5,660,861 A | 8/1997 | Jao et al. |
| 5,670,546 A | 9/1997 | Park et al. |
| 5,688,830 A | 11/1997 | Berger et al. |
| 5,712,277 A | 1/1998 | Nakamura-Craig et al. |
| 5,723,489 A | 3/1998 | Sher et al. |
| 5,741,818 A | 4/1998 | Dimmock |
| 5,849,737 A | 12/1998 | Chaplan et al. |
| 5,891,849 A | 4/1999 | Amstutz et al. |
| 5,905,069 A | 5/1999 | Borsook et al. |
| 5,942,510 A | 8/1999 | Floyd et al. |
| 5,945,454 A | 8/1999 | Peverello et al. |
| 6,113,915 A | 9/2000 | Aoki et al. |
| 6,180,624 B1 | 1/2001 | Hill |
| 6,187,338 B1 | 2/2001 | Caruso et al. |
| 6,207,685 B1 | 3/2001 | Lallemont et al. |
| 6,242,488 B1 | 6/2001 | Bueno et al. |
| 6,281,211 B1 | 8/2001 | Cai et al. |
| 6,290,986 B1 | 9/2001 | Murdock et al. |
| 6,303,819 B1 | 10/2001 | Peverello et al. |
| 6,326,374 B1 | 12/2001 | Magnus et al. |
| 6,326,385 B1 | 12/2001 | Wickendon et al. |
| 6,372,792 B1 | 4/2002 | Chouinard |
| 6,479,484 B1 | 11/2002 | Lan et al. |

(Continued)

FOREIGN PATENT DOCUMENTS

DE  198 02 237 A1  7/1999

(Continued)

OTHER PUBLICATIONS

Shailen et. al. (Expert Opinion on Drug Discovery (2006) 1:341-352).*

(Continued)

*Primary Examiner* — Marcos Sznaidman
(74) *Attorney, Agent, or Firm* — Dechert LLP

(57) ABSTRACT

There is disclosed a pharmaceutical composition comprising gabapentin or an analogue thereof (pregabalin or tiagabine) and an α-aminoamide and its analgesic use. A synergistic effect of the respective analgesic activities without concomitant increase of side effects was observed.

8 Claims, No Drawings

U.S. PATENT DOCUMENTS

| | | |
|---|---|---|
| 6,500,825 B2 | 12/2002 | Lan et al. |
| 7,091,210 B2 | 8/2006 | Lan et al. |
| RE40,259 E | 4/2008 | Pevarello et al. |
| 2004/0248978 A1 | 12/2004 | Salvati |
| 2006/0079570 A1 | 4/2006 | Salvati et al. |
| 2007/0093495 A1 | 4/2007 | Ruggero et al. |
| 2007/0203182 A1 | 8/2007 | Besana et al. |
| 2008/0096965 A1 | 4/2008 | Barbanti et al. |

FOREIGN PATENT DOCUMENTS

| | | |
|---|---|---|
| EP | 0415143 A1 | 6/1991 |
| EP | 0 525 360 A2 | 2/1993 |
| EP | 0200101 A2 | 10/1996 |
| EP | 1 083 164 A1 | 3/2001 |
| EP | 1 229 332 A2 | 8/2002 |
| FR | 2756738 A1 | 12/1998 |
| GB | 1140748 | 1/1969 |
| GB | 2059963 A | 4/1981 |
| WO | WO 98/03167 A1 | 1/1988 |
| WO | WO 90/14334 | 11/1990 |
| WO | WO 94/22808 | 10/1994 |
| WO | WO 94/22809 | 10/1994 |
| WO | WO 96/40628 | 12/1996 |
| WO | WO 97/05102 | 2/1997 |
| WO | WO 97/05111 | 2/1997 |
| WO | WO 98/07447 A1 | 2/1998 |
| WO | WO 98/08842 A1 | 3/1998 |
| WO | WO 98/19674 A2 | 5/1998 |
| WO | WO 98/19998 | 5/1998 |
| WO | WO 98/19674 A3 | 7/1998 |
| WO | WO 98/28255 A1 | 7/1998 |
| WO | WO 98/43964 | 10/1998 |
| WO | WO 98/47869 | 10/1998 |
| WO | WO 99/12537 A1 | 3/1999 |
| WO | WO 99/26614 | 6/1999 |
| WO | WO 99/35123 A1 | 7/1999 |
| WO | WO 99/35125 A1 | 7/1999 |
| WO | WO 99/37296 A1 | 7/1999 |
| WO | WO 99/39712 | 8/1999 |
| WO | WO 99/44610 A1 | 9/1999 |
| WO | WO 99/61408 A1 | 12/1999 |
| WO | WO 00/02562 A1 | 1/2000 |
| WO | WO 00/02592 A1 | 1/2000 |
| WO | WO 00/53225 A1 | 9/2000 |
| WO | WO 00/57877 A1 | 10/2000 |
| WO | WO 00/61188 A1 | 10/2000 |
| WO | WO 0061188 A1 * | 10/2000 |
| WO | WO 01/07037 A1 | 2/2001 |
| WO | WO 01/45684 A2 | 6/2001 |
| WO | WO 0145684 A2 * | 6/2001 |
| WO | WO 01/98779 A2 | 12/2001 |
| WO | WO 03/020273 A2 | 3/2003 |

OTHER PUBLICATIONS

Rosner et. al. (Clin. J. Pain (1996) 12:56-58).*
Faravelli et. al. (Program No. 454.4 2000 Neuroscience Meeting Planner. New Orleans, LA: Society for neuroscience, 2000.*
Chong, MS, et al, "Anticonvulsants for the management of pain", Pain Reviews 2000, 7, pp. 129-147.
Czuczwar, Stanislaw J., "The New Generation of GABA Enhancers Potential in the Treatment of Epilepsy", CNS Drugs 2001. pp. 339-350.
Anonymous, "Cambridge NeuroScience's grant for channel blockers," SCRIP World Pharmaceutical News 1870:8 (1993).
Anonymous, "Neurogen Licenses National Institutes of Health (NIH) anticonvulsants," SCRIP World Pharmaceutical News 1773:14 (1992).
A Wouters (ed.), Proceedings, XIVth International Symposium on Medicinal Chemistry, Maastricht, The Netherlands, Sep. 8-12, 1996, Elsevier Science B.V. (Amsterdam), (cover, front matter, table of contents, index of authors, subject index, Stanford University Libraries date stamp). Copyright 1997; date stamped Aug. 24, 1998, Swain Library, Stanford University.
Bensimon, G., et al., "A Controlled Trial of Riluzole in Amyotrophic Lateral Sclerosis," New Engl. J. Med. 330:585-591 (1994).
Brown, C.M., et al., "Neuroprotective properties of Lifarizine compared with those of other agents in a mouse model of focal cerebral ischaemia," British J. Pharmacol. 115:1425-1432 (1995).
Catterall, W.A., "Common modes of drug action on $Na^+$ channels: Local anesthetics, antiarrhythmics and anticonvulsants," Trends Pharmacol. Sci. 8:57-65 (1987).
Catterall, W.A., "Neurotoxins that Act on Voltage-Sensitive Sodium Channels in Excitable Membranes," Ann. Rev. Pharmacol. Toxicol. 20:15-43 (1980).
Catterall, W.A., "Structure and Function of Voltage-Sensitive Ion Channels," Science 242:50-61 (1988).
Complaint, Civil Action No. 1:07-cv-00487 (Mar. 12, 2007).
Denicoff, K.D., et al., "Efficacy of Carbamazepine Compared With Other Agents: A Clinical Practice Survey," J. Clin. Psychiatry 55:70-76 (1994).
Decision, Preliminary Motions, Bd.R. 125, interference No. 105,394 (2007).
Dimmock, J.R., et al., "(Aryloxy)aryl Semicarbazones and Related Compounds: A Novel Class of Anticonvulsant Agents Possessing High Activity in the Maximal Electroshock Screen," J. Med. Chem. 39:3984-3997 (1996).
Dostert et al., "New anticonvulsants with selective MAO-B inhibitory activity," European Neuropsychopharmacology, 1(3):317-319 (Sep. 1991).
Elrifi et al., "Request for ex parte reexamination of U.S. patent No. 6,479,484 B1," filed Jul. 2, 2003 on behalf of Newron Pharmaceuticals, SpA.
Fariello et al., "Preclinical evaluation of PNU-151774E as a novel anticonvulsant," J. Pharmacol. Exp. Ther. 285(2):397-403 (May 1998).
Fields, "Peripheral neuropathic pain: an approach to management," in PD Wall and R Melack (eds.), Textbook of Pain, $3^{rd}$ ed., Churchill Livingstone, pp. 991-996 (1994).
(First) Declaration of Robert A. McArthur, Pevarello Exhibit 2036, interference 105,394 (2006).
First Declaration of Stephen G. Waxman, M.D., Ph.D., PX 2003, interference No. 105,394 (2006).
Galer BS, "Neuropathic pain of peripheral origin: advances in pharmacologic treatment," Neurol. 45:S17-S25, 1995.
Guieu et al., "Central analgesic effect of valproate in patients with epilepsy," Seizure 2:147-150 (1993).
Graham, S.H., et al., "Neuroprotective Effects of a Use-Dependent Blocker of Voltage-Dependent Sodium Channels, BW619C89, in Rat Middle Cerebral Artery Occlusion," J. Pharmacol. Exp. Ther. 269:854-859 (1994).
Hammer et al., "Effect of Riluzole on acute pain and hyperalgesia in humans," Brit. J. Anaesthesia 82(5):718-22 (1999).
Judgment, Preliminary Motions, Bd.R. 127, interference No. 105,394 (2007).
Kingery, "A critical review of controlled clinical trials for peripheral neuropathic pain and complex regional pain syndromes," Pain 73:123-139 (1997).
Lunardi et al., "Clinical effectiveness of lamotrigine and plasma levels in essential and symptomatic trigeminal neuralgia," Neurology 48(6) 1714-1717 (1997).
McQuay et al., "Anticonvulsant drugs for management of pain: a systematic review," BMJ 311:1047-1052 (Oct. 21, 1995).
Memorandum Opinion and Order, interference No. 105,394 (2007).
Nakamura-Craig et al., "Effect of lamotrigine in the acute and chronic hyperalgesia induced by $PGE_2$ and in the chronic hyperalgesia in rats with streptozocin-induced diabetes," Pain 63:33-37 (1995).
Notice of Dismissal With Prejudice, Civil Action No. 1:07-cv-00487 (Jul. 25, 2007).
Official action, counterpart Brazilian application (to RE40,259) No. PI 9814548-7 (translation).
Pevarello et al., "Synthesis and Anticonvulsant Activity of a New Class of 2-Arylalkyl amino alkanide Derivatives", J. Med. Chem. 41:5 79-590 (1998).
Pevarello et al., "Stereoselectivity, sigma binding and sodium channel blocking activity of 2-aminopropanamide anticonvulsants," from

*Abstracts*, XIVth International Symposium on Medicinal Chemistry, Maastricht, the Netherlands, Sep. 8-12, 1996 (4 pages) (Sep. 8, 1996).

Pevarello et al., "Stereoselectivity, sigma binding and sodium channel blocking activity of 2-amino propanamide anticonvulsants." (3 pages) (Sep. 12, 1996).

Puig et al., "Formalin-evoked activity in identified primary afferent fibers: systemic lidocaine suppresses phase-2 activity," *Pain* 64:345-355 (1995).

Salvati et al.," Anticonvulsant profile of FCE26743A (PNU-151774), a novel 2-aminopropionamide derivative. Society for Neuroscience. Washington. Nov. 15-21, 1996." (4 pages) (Nov. 21, 1996, date solely for purpose of initial consideration).

Shibata et al., "Modified formalin test: characteristic biphasic pain response," *Pain* 38:347-352 (1989).

Stys, P.K., et al., "Ionic Mechanism of Anoxic Injury in Mammalian CNS White Matter: Role of $Na_+$ Channels and $Na^+$-$Ca^{2+}$ Exchanger," *J. Neurosci.* 12:430-439 (1992).

Supplemental data, Vieth et al., "Characteristic Physical Properties and Structural Fragments of Marketed Oral Drugs," *J. Med. Chem.* 47:224-232 (2004) (downloaded Aug. 20, 2007 from http://pubs.acs.org) (excerpted fields).

Tanelian et al., "Neuropathic pain can be relieved by drugs that are use-dependent sodium channel blockers: lidocaine, carbamazepine, and mexiletine," *Anesthesiol* 74(5):949-951 (1991).

Tanelian et al., "Sodium channel-blocking agents: their use in neuropathic pain conditions," *Pain Forum* 4(2):75-80 (1995).

Taylor, C.P. and Meldrum, B.S., "$Na^+$ channels as targets for neuroprotective drugs," *Trends Pharmacol Sci.* 16:309-316 (1995).

Tjolsen et al., "The formalin test: an evaluation of the method," *Pain* 51:5-17 (1992).

Vaghi et al., "Neuroprotective effect of PNU-151774E, a new anticonvulsant compound, in the model of global ischaemia in gerbils." (5 pages) (Oct. 30, 1997, date solely for purpose of initial consideration).

Varasi et al., "Synthesis and anticonvulsant activity of new benzyloxybenzylacetamide derivatives," from *Abstracts, XII$^{th}$ International Symposium on Medicinal Chemistry*, Basel, Switzerland, Sep. 13-17, 1992 (2 pages) (1992).

Varasi et al., "Synthesis and anticonvulsant activity of new benzyloxybenzylacetamide derivatives" (2 pages) (1992).

Vieth et al., "Characteristic Physical Properties and Structural Fragments of Marketed Oral Drugs," *J. Med. Chem.* 47:224-232 (2004).

Webber, "Observations under article 115 EPC", filed Nov. 19, 2002 in EP 98958114.5 (EP 1032377) on behalf of Newron Pharmaceuticals, SpA.

Wilton, "Tegretol in the treatment of diabetic neuropathy," *S. Afr. Med. J.* 48(20):869-872 (1974).

Woolf et al., "The systemic administration of local anaesthetics produces a selective depression of C-afferent fibre evoked activity in the spinal cord," *Pain* 23(4):361-374 (1985).

"About Post-Herpetic Neuralgia", www.aftershingles.com, 2000.

Attal , N., "Antiepileptic drugs in the treatment of neuropathic pain," *Exp. Rev.* Neurotberapeutics 1:199-206. Future Drugs Ltd. (2001).

Backonja et al., "Gabapentin for the symptomatic treatment of painful neuropathy in patients with diabetes mellitus. A randomized controlled trial", JAMA 20 2 80 (2 1): 1831-1836, Dec. 1998).

Bennett. G.J., "Neuropathic Pain: New Insights, New Interventions, " *Hospital* practice JJ:95-98,101-104,107-110,113-114, The McGraw-Hill Companies, Inc. (1998).

Beydoun, A., "Postherpetic Neuralgia: Role of Gabapentin and Other Treatment Modalities," *Epilepsia* 40 (*Suppl.* 6):551-556, Lippincott Williams & Wilkins (Oct. 1999).

Blinder, B.J. et al., "Advances in Mood Stabilizing Medications." *West. J. Med.*169:39-40. BMJ Publishing (1998).

Borowicz, K.K. et al., "Effect of Gabapentin on the Anticonvulsant Activity of Antiepileptic Drugs against Electroconvulsions in Mice: An Isobolographic Analysis." *Epilepsia* 43:956-963. Blackwell Publishing. Inc. (2002).

Boyce, S. et al,. "Selective NMDA NR2B antagonists induce antinociception without motor dysfunction: correlation with restricted localisation of NR2B subunit in dorsal horn," *Neuropharmacology* 38:611-623. Pergamon and Elsevier Science Ltd. (May 1999).

Bryans, J.S., and Wustrow, O.J., "3-Substituted GABA Analogs with Central Nervous System Activity, A Review," *Med. Res. Rev.* 19:149-177. John Wiley & Sons, Inc. (Mar. 1999).

Buchan, A.M., et al., AMPA Antagonists: Do They Hold More Promise for Clinical Stroke Trials Than NMDA Antagonists?, *Supplement I, Stroke* 24:1148-1152. American Heart Association (1993).

Butler et al., "A limited arthritic model for chronic pain studies in the rat" Pain; 48: 73-81, 1992.

Canavero et al., "The riddle of trigeminal neuralgia," *Pain* 60:229-23. Elsevier Science B.V. (1995).

Carrazana et al., "Alternative uses of lamotrigine and gabapentin in the treatment of trigeminal neuralgia." *Neurology* 50:1192. The American Academy of Neurology (Apr. 1998).

Chapman, V., et al., "Effects of systemic carbamazepine and gabapentin on spinal neuronal responses in spinal nerve ligated rats," *Pain* 75:261-272, Elsevier Science B.V. (Apr. 1998).

Creveling et al , Batrachotoxin-Induced Depolarization and ($^3$H)Batrachotoxinin-A 20α-Benzoate Binding in a Vesicular Preparation from Guinea Pig Cerebral Cortex, *Mol. Pharmacal.* 23:350-358, The American Society for Pharmacology and Experimental Therapeutics (1983).

Czuczwar et al., "Felbamate, Gabapentin and Topiramate as Adjuvant Antiepileptic Drugs in Experimental Models of Epilepsy," *Polish J. Pharmacal.* 53:65-68, Polish Academy of Sciences (2001).

De Sarro et al., "Gabapentin Potentiates the Antiseizure Activity of Certain Anticonvulsants in DBA/2 Mice," *Eur. J. Pharmacal.* 349:179-185, Elsevier Science (1998).

Dichter et al., "Drug Therapy, New Antiepileptic Drugs." *New Engl. J. Med.* 334:1583-1590. Massachusetts Medical Society (1996).

Donnadieu et al., Pain Relief, *Presse Medicale*, (1998), 27/39, 2062-2069.

Dunham, N.W. et al., "A Note on the Simple Apparatus for Detecting Neurological Deficit in Rats and Mice," *J. of the American Pharmaceutical Association*, 1957, 46 (3) 208-209.

Field et al, "Gabapentin and pregabalin, but not morphine and amitriptyline, block both static and dynamic components of mechanical allodynia induced by streptozocin in the rat." *Pain* 80:391-398, Elsevier Science B. V. (Mar. 1999).

Field et al., "Evaluation of Gabapentin and S- (+)-3-Isobutylgaba in a rat model of postoperative pain", *J. Pharmacol. Exp. Ther.*; 282 (3): 1242-4, (1997).

Goldberg et al., "Focus on Gabapentin." *Focus* 8:1-6, Priory Lodge Education Ltd. (1997) from http://www.priory.com/focus8.htm.

Graham et al., "A Dose-Response Study of Neuroprotection Using the AMPA Antagonist NBQx in Rat Focal Cerebral Ischemia." *J. Pharmacol. Exp. Therap.* 276:1-4, Williams & Wilkins (1996).

Gurney, et al., "Benefit of Vitamin E, Riluzole, and Gabapentin in a Transgenic Model of Familial Amyotrophic Lateral Sclerosis," *Am. Neural.* 39,147-157, The American Neurological Association (1996).

Hamill et al., "Improved Patch-Clamp Techniques for High-Resolution Current Recording from Cells and Cell-Free Membrane Patches," *Pfluegers Arch 391*, 85-100. Springer International (1981).

Hoekstra et al., "Chemical Development of C1-1008, an Enantiomerically Pure Anticonvulsant," *Org. Process Res. Dev.* 1:26-38, American Chemical Society and Royal Society of Chemistry (1997).

Hunskaar, S. et al., "Formalin test in mice, a useful technique for evaluating mild analgesics." *J. Neurosci. Methods* 14:69-76, Elsevier Science Publishers B.V. (1985).

International Search Report for PCT/EP02/028910 dated Mar. 13, 2003.

Iwasaki. Y., et al., "CNQX prevents spinal motor neuron death following sciatic nerve transection in newborn rats." *J. Neuro Sci.* 134:21-25, Elsevier Science B.V. (1995).

Kim, S.H. et al., "An experimental model for peripheral neuropathy produced by segmental spinal nerve ligation in the rat." *Pain 50*:355-363, Elsevier Science Publishers B.V. (1992).

Kudoh, A., et al., "Effect of Carbamazepine on Pain Scores of Unipolar Depressed Patients with Chronic Pain: A Trial of Off-On-Off-On Design," *Clin. J. Pain 14*:61-65, Lippincott-Raven Publishers (1998).

Low, P.A.. et al., "Symptomatic Treatment of Painful Neuropathy," *JAMA 280*:1863-1864, The American Medical Association (Dec. 19981).

Magnus. L. "Nonepileptic Uses of Gabapentin," *Epilepsia 40 (Suppl. 6)*:566-572, Lippincott Williams & Wilkins (Oct. 1999).

Mounsey et al., "Herpes Zoster and Postherpetic Neuralgia", *American Family Physician*, 2005, vol. 72. No. 6, pp. 1075-1080.

Nicolaus, B. J. R., "Symbiotic Approach to Drug Design," *Decision Making in Drug Research, Raven Press*, 1983, pp. 173-186.

Nicholson. B. "Gabapentin use in neuropathic pain syndromes," *Dolor 14*:243-250, Publicaciones Permanyer (1999).

Office Action for U.S. Appl. No. 10/541,195 mailed on Dec. 14, 2007.

Ohizumi, Y., et al., "Specific Inhibitors of [$^3$H1 Saxitoxin Binding to Skeletal Muscle Sodium Channels by Geographutoxin II, a Polypeptide Channel Blocker," *J. Biol. Chem.* 261:6149-6152. The American Society of Biological Chemists. Inc.(1986).

Pan et al., "Gabapentin suppresses ectopic nerve discharges and reverses allodynia in neuropathic rats", *J.Pharmacol. Exp. Ther.*; 288 (3): 1026-1030, (1999).

Przesmycki, K. et al., "Isobolographic Analysis of Interaction Between Intrathecal Morphine and Clonidine in the Formalin Test in Rats," *Eur. J. of Pharmacology*, 337: 11-17 (1997).

Rosenberg, J. M. et al., "The Effect of Gabapentin on Neuropathic Pain," *Clin. J. Pain 13*:251-255. Lippincott-Raven Publishers (1997).

Rosner et al., "Gabapentin adjunctive therapy in neuropathic pain states", 10 *Clin. J. Pain*; 12 (1) : 56-8, 1996.

Rowbotham et al., "Gabapentin for the treatment of postherpetic neuralgia. A randomized controlled trial", *JAMA* 280: 1837-1842, *The Great American Medical Association* (Dec. 2, 1998).

Sheardown, M.J., et al., AMPA, but not NMDA, receptor antagonism is neuroprotective in gerbil global ischaemia, even when delayed 24 h. *Sur. J. Pharmacol.* 236:347-353. Elsevier Science Publishers B.V. (1993).

Sist, T.C. et al., "Experience With Gabapentin for Neuropathic Pain in the Head and Neck: Report of Ten Cases," *Reg. Anesth.* 22:473-478, The American Society of Regional Anesthesia (1997).

Solaro, C., et al., "A patient with multiple sclerosis and Down's syndrome with a rare paroxysmal symptom at onset." *Eur. J. Neurol.* 6:505-507. Lippincott Williams & Wilkins. (Jul. 1999).

Tallarida, R.J., "Statistical Analysis of Drug Combinations for Synergism," *Pain*, 49: 93-97, 1992.

Tallarida, R. J. et al., "Efficient Designs for Studying Synergistic Drug Combinations," *Life Sciences*, vol. 61, n. 26, 417-425, 1997.

"Treatment of Trigeminal Neuralgia at Mayo Clinic", www.mayoclinic.org. 2006.

Tremont-Lucats at al., "Anticonvulsants for neuropathic 30 pain syndromes: mechanisms of action and place in therapy.", *Drugs*, 60 (5): 1029-52, (2000).

"Trigeminal Neuralgia", www.enwikipedia.org, 2006.

U.S. Appl. No. 60/126,553, Hogenkamp et al., filed Mar. 26, 1999.

Verdoorn, T.A., et al.., "Functional Properties of Recombinant Rat GABAA Receptors Depend upon Subunit Composition." *Neuron 4*:919-928. Cell Press (1990).

Victor, M. et al ,. "Chapter 352: Diseases of the Cranial Nerves." in *Harrison's Principles of Internal Medicine 11*:2035-2040, Braunwald. et al., eds., McGraw-Hill Inc. (1987).

Wamil, A.W., and McLean. M.J., "Limitation by gabapentin of high frequency action potential firing by mouse central neurons in cell culture." *Epilepsy Res. 17*:1-11. Elsevier Science B.V. (1994).

Wrathall, J.R., et al., Amelioration of Functional Deficits from Spinal Cord Trauma with Systemically Administered NBQX, an Antagonist of Non-N-methyl-D-aspartate receptors,—Exp. *Neurology* 137:119-126, Academic Press, Inc. (1996).

Yoon, M.H., and Yaksb, T.L., "Evaluation of Interaction between Gabapentin and Ibuprofen on the Formalin Test in Rats." *Anesthesiology 91*:1006-1013. Lippincott Williams & Wilkins. Inc. (Oct. 1999).

Zagaria, M.A., "Posthepetic Neuralgia", *US. Pharmacist*, 2002, vol. 27, No. 10.

Bennet, G. J., 1997, "Neuropathic Pain: An Overview," in *Molecular Neurobiology of Pain*, David Borsook, Ed., Progress in pain research and management, vol. 9 (International Association for the Study of Pain Press, Seattle, USA) 109-113.

Faravelli et al., 2000, NW-1029 is a Novel Na+ Channel Blocker with Analgesic Activity in Animal Models. Program No. 454.4. Presentation No. 464.9. Society for Neuroscience Annual Meeting. New Orleans, LA.

Hunter et al., 1997. The effect of novel anti-epileptic drugs in rat experimental models of acute and chronic pain. European Journal of Pharmacology 324, No. 2-3 (April): 153-160.

Lu et al., 1999. Gabapentin attenuates nociceptive behaviors in an acute arthritis model in rats. J. Pharmacol. Exp. Ther. 290(1):214-9.

Veneroni et al., 2003. Anti-allodynic effect of NW-1029, a novel Na(+) channel blocker, in experimental animal models of inflammatory and neuropathic pain. Pain 102, No. 1-2 (March): 17-25.

Westlund et al., 1998. S-(+)-Isobutylgaba and Its Stereoisomer Reduces the Amount of Inflammation and Hyperalgesia in an Acute Arthritis Model in the Rat. J. Pharmacol. Exp. Ther. 285:533-538.

Larsen and Arnt, "Reduction in Locomotor Activity of Arthritic Rats as Parameter for Chronic Pain: Effect of Morphine, Acetylsalicylic Acid and Ctalopram," *Acta pharmacol. Et toxicol.* 51:345-351 (1985).

\* cited by examiner

PHARMACEUTICAL COMPOSITION COMPRISING GABAPENTIN OR AN ANALOGUE THEREOF AND AN α-AMINOAMIDE AND ITS ANALGESIC USE

CROSS-REFERENCE TO RELATED APPLICATIONS

This application is a National Stage entry of International Application No. PCT/EP02/08910, filed Aug. 9, 2002, which claims the benefit of European patent application no. 01121069.7, filed Sep. 3, 2001, the entire specification claims and drawings of which are incorporated herewith by reference.

The present invention relates to a pharmaceutical composition comprising gabapentin or an analogue thereof and an α-aminoamide and its analgesic use. More particularly, this invention is directed to a pharmaceutical composition comprising gabapentin or pregabalin or tiagabine, and an α-aminoamide useful in the treatment of pain.

Pain is commonly alleviated by administering analgesic drugs which act to decrease the sensation of pain by elevating the pain threshold, and/or altering its perception.

Although a large number of pain syndromes are treated by available therapies, chronic neuropathic pain syndromes that follow peripheral nerve damage have been found to have a much reduced sensitivity to the two major classes of analgesics, opioids and non steroidal antiinflammatory drugs (NSAID).

In the search for alternative forms of treatment, anticonvulsants have emerged as possible pharmacological interventions (McQuay et al., "Anticonvulsant drug for the management of pain: a systematic review", Br. Med. J., 311: 1047, 1995).

Among the new generation of antiepileptic drugs (AED) used for the treatment of neuropathic pain, 1-(aminomethyl) cyclohexaneacetic acid, also known as gabapentin (hereinafter GBP), an aminoacid structurally related to γ-aminobutyric acid (hereinafter GABA), occupies a prominent position together with its structural analogues, such as pregabalin (Tremont at al., "Anticonvulsants for neuropathic pain syndromes: mechanisms of action and place in therapy.", Drugs, 60 (5): 1029-52, 2000) and tiagabine (Field at al., "Evaluation of Gabapentin and S-(+)-3-Isobutylgaba in a rat model of postoperative pain", J. Pharmacol. Exp. Ther.; 282 (3): 1242-4, 1997) as to frequency and broadness of use.

It has been reported that GBP is active in various animal models of pain, where it blocks the late tonic phase of nociception induced by formalin, reverses allodynia of rats with neuropathy induced by partial ligation of the sciatic nerve (Pan et al., "Gabapentin suppresses ectopic nerve discharges and reverses allodynia in neuropathic rats", J. Pharmacol. Exp. Ther.; 288 (3): 1026-30, 1999), as well as clinically, where it alleviates neuropathic pain, diabetic neuropathy and postherpetic neuralgia (Rosner et al., "Gabapentin adjunctive therapy in neuropathic pain states", Clin. J. Pain; 12 (1): 56-8, 1996).

However, GBP produces a cohort of side effects in patients such as ataxia, dyspnea, nausea and sedation which limits its usefulness (FDA approved labelling text, NDA 21-216, NDA 20-235/S-015, NDA 20-882/S-002, NDA 21-129/S-005; Rowbotham et al., "Gabapentin for the treatment of postherpetic neuralgia. A randomized controlled trial", JAMA 280 (21): 1831-1836, 1998; Backonja et al., "Gabapentin for the symptomatic treatment of painful neuropathy in patients with diabetes mellitus. A randomized controlled trial", JAMA 280 (21): 1837-1842, 1998).

On this ground, it would be desirable to find other compounds with antinociceptive mechanism of action different from and/or complementary to the one of GBP or its analogues so that lower doses of GBP or its analogues could be used limiting the known side effects, yet allowing maintenance of its analgesic properties or even better potentiating them.

Although GBP was developed as a structural GABA analogue, it does neither appear to have direct "GABA-ergic" action, nor does it affect GABA uptake or metabolism. To explain the antihyperalgesic effect of GBP, preliminary evidence points to the possible effect of GBP on the voltage dependent $Ca^{++}$ channels by interaction with the α/2-δ subunit. Experimental evidence supports the involvement of $Ca^{++}$ channels in the pathophysiology of pain. Thus, the action of GBP on these channels may be a significant contributor to its antinociceptive effect.

Anticonvulsant drugs such as gabapentin, have been combined with non-toxic blockers for the N-methyl-d-aspartate (NMDA) receptor. Such compositions have been described as useful in the treatment of neuropathic pain. For example, WO 98/07447 discloses the combination of a neuropathic pain alleviating amount of an anticonvulsant drug, including gabapentin, lamotrigine, valproic acid, topiramate, famotidine, phenobarbital, diphenylhydantoin, phenyloin, mephenyloin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethedione, phenyloin sodium, valproate sodium, clobazam, sulthiame, dilantin, diphenylan or L-5-hydroxytrytophan and an anticonvulsant potentiating amount of a non-toxic blocker for the NMDA receptor. This reference, however, does not teach any synergistic effect of the disclosed compositions.

Anticonvulsant drugs combined with NSAIDs or narcotic analgesics have also been described as useful in the treatment of pain. WO 99/12537 discloses a composition of the anticonvulsant compounds gabapentin or pregabalin in combination with the NSAID naproxen or with narcotic analgesics. Combinations of anticonvulsants and other drugs with opioid analgesics have been suggested (Donnadieu, S., et al., Pain Relief, Presse Medicale, 1998, 27/39, 2062-2069). These references, however, also do not teach any synergistic effect of the disclosed compositions.

Combinations of anticonvulsant drugs, including GBP, with the centrally acting analgesic tramadol, i.e. (1R,2R or 1S,2S)-2-[(dimethylamino)methyl]-1-[3-methoxyphenyl] cyclohexanol are described in WO 01/13904.

WO 00/61188 discloses a pharmaceutical composition comprising a sodium channel blocker and gabapentin or pregabalin or salts or combinations thereof; the composition is effective in treating, preventing or ameliorating chronic pain or convulsions. Among the sodium channel blockers, a number of aminoamides are cited, for instance the ones disclosed in U.S. Pat. No. 5,449,692 (WO 94/22809), WO 97/05102, U.S. Pat. No. 5,446,066 (WO 94/22808) and U.S. Pat. No. 5,236,957 (WO 90/14334), although a composition comprising them is never exemplified, whereas the synergistic antiallodynic effect of gabapentin and the sodium channel blocker 4-(4'-fluoro-phenoxy)benzaldehyde semicarbazone, in the Chung model of neuropathic pain in rats, is therein illustrated.

It is an object of the present invention to provide a composition comprising an $Na^+$ channel blocker α-aminoamide and GBP, or pregabalin or tiagabine, having improved properties for the therapy of pain.

It is also an object of the present invention to provide a composition comprising an α-aminoamide and GBP, or pregabalin or tiagabine, wherein the combination of said compounds shows a synergistic effect, while using less of each of said compounds.

Further, the Applicant noticed that not all the sodium channel blockers active in a model of chronic pain are synergic to gabapentin.

It has now been found that only some known α-aminoamides or a pharmaceutically acceptable derivative thereof, endowed with analgesic activity, combined with GBP or pregabalin or tiagabine, or a pharmaceutically acceptable derivative thereof, significantly potentiate the analgesic or antinociceptive properties of GBP (or pregabalin or tiagabine), surprisingly providing an actual synergistic effect in comparison with the respective activities, and therefore succeeding in dramatically limiting the side effects of GBP (or pregabalin or tiagabine) by allowing to reduce its pharmaceutically effective amount to an unexpectedly lower dosage.

The pharmaceutical composition of the present invention comprises a combination of an α-aminoamide and GBP (or pregabalin or tiagabine), wherein the α-aminoamide and GBP (or pregabalin or tiagabine) are present in a ratio based on a fraction of their respective $ED_{50}$ values, which ratio is from about 1:1 to about 30:1 or from about 1:1 to about 1:30; preferably from about 1:1. to about 9:1 or from about 1:1 to about 1:9; most preferably from about 1:1 to about 3:1 or 1:1 to about 1:3.

According to a first aspect of the present invention, a pharmaceutical composition is provided comprising gabapentin, or pregabalin or tiagabine or a pharmaceutically acceptable derivative thereof, and an α-aminoamide selected from the group consisting of (S)-(+)-2-[4-(2-fluorobenzyloxy)benzylamino]propanamide (internal code: NW-1029), (R)-(−)-2-[4-benzyloxybenzylamino]-3-phenyl-N-methylpropanamide, (internal code: NW-1037) and (S)-(+)-2-[4-(3-fluorobenzyloxy)-benzylamino]-N-methyl-propanamide (internal code: NW-1043);

if the case, either as a single isomer, or as a mixture thereof, or a pharmaceutically acceptable derivative thereof;

wherein the α-aminoamide and gabapentin or pregabalin or tiagabine or the pharmaceutically acceptable derivatives thereof, are present in a ratio based on a fraction of their respective $ED_{50}$ values, which ratio ranges from about 1:1 to about 30:1 or from about 1:1 to about 1:30, respectively.

Preferably, the above defined α-aminoamide and GBP (or pregabalin or tiagabine) comprised in the pharmaceutical composition of the present invention are present in a ratio based on a fraction of their respective $ED_{50}$ values, which ratio ranges from about 1:1 to about 9:1 or from about 1:1 to about 1:9, respectively; most preferably the ratio ranges from about 1:1 to about 3:1 or 1:1 to about 1:3, respectively.

A second aspect of the invention concerns the use of the above defined pharmaceutical composition for the preparation of a medicament for the treatment of a condition of pain.

A further aspect of this invention relates to a method for treating a condition of pain in a mammal, including humans, in need thereof comprising administering to the mammal a therapeutically effective dose of the above defined pharmaceutical composition.

Particularly, the mammal in need of the said treatment is administered a dose of the pharmaceutical composition which ranges from about 0.05 to about 50 mg/die per kg of body weight; the pharmaceutical composition comprises gabapentin and an α-aminoamide selected from the group consisting of (S)-(+)-2-[4-(2-fluorobenzyloxy)benzylamino] propanamide, (R)-(−)-2-[4-benzyloxybenzylamino]-3-phenyl-N-methylpropanamide, and (S)-(+)-2-[4-(3-fluorobenzyloxy)-benzylamino]-N-methyl-propanamide, if the case, either as a single isomer, or as a mixture thereof, or a pharmaceutically acceptable derivative thereof, in a ratio of gabapentin and the α-aminoamide, based on a fraction of their respective $ED_{50}$ values, of from about 1:1 to about 30:1 or from about 1:1 to about 1:30, more preferably of from about 1:1 to about 9:1 or from about 1:1 to about 1:9, most preferably of from about 1:1 to about 3:1 or from about 1:1 to about 1:3.

Neuropathic and chronic pain conditions in a mammal, including humans, can thus be alleviated and treated. Examples of conditions of mammalian pain which can be treated by the composition of the invention include centrally mediated pain, peripherally mediated pain, structural or soft tissue injury related pain, progressive disease related pain and neuropathic pain states, all of which would include acute pain such as caused by acute injury, trauma or surgery;

In particular, examples of pain conditions that can be treated by the composition of the invention include peripheral neuropathies, such as trigeminal neuralgia, post-herpetic neuralgia, diabetic neuropathy, or other metabolic neuropathies, glossopharyngeal neuralgia, radiculopathy, dental pain, cluster, migraine and any of the type of vascular headaches and neuropathy secondary to metastatic infiltration, adiposis dolorosa and burn pain; central pain conditions following stroke, injury accidental or surgically or otherwise produced thalamic lesions and multiple sclerosis. Examples of pain inflammatory conditions that can be treated by the composition of the invention include rheumatoid arthritis, ankylosing spondylitis, osteoarthritis, bursitis, tendinitis and acute gouty arthritis.

"Treatment" as used herein covers any treatment of a condition in a mammal, particularly a human, and includes:

(i) preventing the disease from occurring in a subject which may be predisposed to the disease, but has not yet been diagnosed as having it;

(ii) inhibiting the condition, i.e., arresting its development; or (iii) relieving the condition, i.e., causing regression of the disease.

Both GBP (or pregabalin or tiagabine) and said α-aminoamides and the pharmaceutically acceptable derivatives thereof are referred in the present description as the "active compounds".

Further, a "pharmaceutically acceptable derivative" of the active compounds is herein meant to include any pharmaceutically acceptable metabolite, bioprecursor and/or pro-drug, i.e. a compound which has a structural formula different from the one of the active compounds and yet is directly or indirectly converted in vivo into a compound having their structural formula, upon administration to a mammal, particularly a human being.

Examples of pharmaceutically acceptable derivatives of the active compounds include acid addition salts with inorganic acids, e.g. nitric, hydrochloric, hydrobromic, sulfuric, perchloric and phosphoric acids and the like, or organic acids, e.g. acetic, propionic, glycolic, lactic, oxalic, malonic, malic, tartaric, citric, succinic, benzoic, cinnamic, mandelic, methanesulfonic, p-toluenesulfonic and salicylic acids and the like.

The α-aminoamides comprised in the composition of the invention and the analgesic activity thereof, in particular against chronic and neuropathic pain in mammals including humans, are disclosed in WO 90/14334 and WO 99/35125, respectively, and can be prepared according to what therein disclosed, said documents being herein incorporated by reference as far as the obtainment of said α-aminoamides is concerned.

In a pharmaceutical composition of the present invention, an α-aminoamide, GBP (or pregabalin or tiagabine), are present in a ratio based on a fraction of their respective $ED_{50}$ values which ratio may vary from about 1:1 to about 30:1 or, reversibly, from about 1:1 to about 1:30; preferably, from about 1:1 to about 9:1 or from about 1:1 to about 1:9; and, more preferably, from about 1:1 to about 3:1 or from about 1:1 to about 1:3, depending upon the desired result.

The expert in the field will understand that, although GBP is preferably employed as one of the active compounds of the composition according to this invention, pregabalin or tiagabine may by used instead of GBP in said composition by applying the same concepts and ideas which form the basis of this invention.

The composition of the invention can be prepared by conventional procedures known in the art, for instance by mixing the active compounds with pharmaceutically, therapeutically inert organic and/or inorganic carrier materials. The composition of the invention can be in liquid form, e.g. in the form of a solution, suspension, emulsion; or in solid form, e.g. tablets, troches, capsules.

Suitable pharmaceutically, therapeutically inert organic and/or inorganic carrier materials useful in the preparation of the composition of the present invention include, for example, water, gelatin, gum arabic, lactose, starch, cellulose, magnesium stearate, talc, vegetable oils polyalkyleneglycols and the like. The pharmaceutical composition of the invention can be sterilized and may contain further components, well known to the skilled in the art, such as, for example, preservatives, stabilizers, wetting or emulsifying agents, e.g. paraffin oil, mannide monooleate, salts to adjust osmotic pressure, buffers and the like.

The pharmaceutical composition of the invention is generally in the form of a dose unit.

Optimal therapeutically effective doses to be administered may be readily determined by those skilled in the art and will vary with the particular combination of an α-aminoamide and GBP (or pregabalin or tiagabine), with the amount of active ingredients used in a synergistic ratio based on a fraction of their respective $ED_{50}$ values, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

In general, a dose unit of the pharmaceutical composition of the invention may contain about 0.2 to 99.8, preferably about 0.5 to 99.5 percent by weight of each of the active compounds, in the whole mixture of the active compounds. The combination of the two active compounds, in general, can be administered to a mammal in need thereof in a wide range of dose from about 0.05 to about 50 mg/die per kg of body weight or, more specifically, to a human patient of an average body weight of 70 kg, in a dose of from about 3.5 mg to about 3500 mg/die.

Further, it is also within the scope of the invention to administer each active compound of the composition of the invention individually. Thus, it is also possible to formulate each of the two active compounds into separate dosage forms, in accordance with conventional procedures known in the art, and to administer them either simultaneously or sequentially.

In other words, the unexpected analgesic activity obtained by the composition of the invention may be achieved by either simultaneous or sequential administration of the active compounds.

Routes of administration of the composition of the invention may be both oral and parenteral. The composition should be administered at least once a day or more frequently, if needed, in relation to the severity of the conditions of the patient. The analgesic effect observed is significantly greater than that which would result from the additive effect of the separate active compounds. The advantages of the antinociceptive potentiation are many, and include a reduction in the dosage of the GBP or pregabalin or tiagabine required to produce analgesia, with a consequent reduction in undesirable side effects.

A single dose of a formulation of a pharmaceutical composition of the invention showing a synergistic activity, therefore, contains a therapeutically effective dose of active ingredient which generally ranges from about 3.5 mg to about 3500 mg of a combination of an α-aminoamide and GBP (or pregabalin or tiagabine); preferably, from about 8 mg to about 400 mg; more preferably, from about 15 mg to about 250 mg; and, most preferably, from about 18 g to about 90 mg. For example, a 20 mg formulation of a pharmaceutical composition comprising GBP ($ED_{50}$=12.40 mg) and NW-1029 ($ED_{50}$=0.82 mg), in a 1:3 ratio, respectively, based on a fraction of their respective $ED_{50}$ values, will contain about 16.7 mg of GBP and about 3.3 mg of NW-1029.

General Methods

Co-administration of equipotent anti-nociceptive doses of different of the above defined α-aminoamides (in particular NW-1029, NW-1037 and NW-1043) and of GBP was investigated in order to show that the composition of the invention produces a synergistic effect greater than the activity shown by each of the active compounds when given alone, and greater than the one that one would expect under simple additivity of the activities of each of the active compounds, without concomitant increase in related side effects. As previously recalled, typical side effects of GBP in animals are motor impairment and ataxia.

The synergistic antiallodynic effect of the composition of the invention and its effect on motor performance were evaluated using the following methods in the rat:

The testing for synergism of the active compounds of the composition of the invention was carried out according to the approach developed by Tallarida, R. J. 1992, Pain, 49: 93-97; Tallarida, R. J. et al. 1997, Life Sciences, Vol. 61, n. 26, 417-425; Przesmycki, K. et al. 1997, Eur. J. of Pharmacology, 337: 11-17.

This procedure involves the determination of the total amount in the mixture that is required to produce a specified synergistic antiallodynic effect at the 50% dose level ($ED_{50mix}$) and the corresponding total amount that would be expected under simple additivity ($ED_{50add}$). Where it is established that $ED_{50mix} < ED_{50add}$ for a specific fixed ratio, then the composition has a synergistic antiallodynic effect. Both the quantities $ED_{50mix}$ and $ED_{50add}$ are random variables. $ED_{50mix}$ was determined from the dose-response curve for a specific fixed ratio of the components; $ED_{50add}$ was calculated from the $ED_{50}$ values for the individual drugs.

$ED_{50mix}$ was then statistically compared to $ED_{50add}$: in the present description, "significantly lower than the theoretical additive value" ($ED_{50add}$) is meant to indicate the experimental $ED_{50}$ value is outside of the 95% Confidence Intervals (CI) of the $ED_{50add}$.

In other words, if the actual $ED_{50mix}$ falls within the C.I. of the theoretical additive $ED_{50add}$, the effect of the composition would be additive; otherwise, if the composition $ED_{50mix}$ is less than the theoretical additive $ED_{50add}$ (i.e. it does not fall within the theoretical C.I.), a significant synergistic interaction between the active compounds occurs.

Therefore, $ED_{50}$ values where considered to differ significantly (P<0.05) from each other, if each $ED_{50}$ value was outside the 95% C.I. of the other.

General method A:

Procedure for Testing the Antiallodynic Effect of the Composition of the Invention The procedure used to detect and compare the synergistic effect of the composition of the present invention for which there is a good correlation with human efficacy for the treatment of pain is measurement of allodynia in the monoarthritic rat model of chronic pain induced by complete Freund's adjuvant (CPA) (see, e.g., Butler et al., "A limited arthritic model for chronic pain studies in the rat", Pain 48:73-81 (1992).

Animals

Adult male Wistar rats (body weight 175-200 g, Harlan-Nossan, Italy) were housed in separate cages with free access to water and standard rat chow at a constant temperature (22±0.5° C.) and relative humidity (60-70%), with a 6.00 am to 6.00 pm light-dark period.

Monoarthritic Model

The inflammation was induced in rats by an intra-plantar injection of complete Freund's adjuvant (CFA, Sigma-100 μl) into left hind paw containing heat-killed and dried *Mycobacterium tuberculosis* in a mixture of paraffin oil and mannide monooleate as emulsifying agent. A group of control animal were injected with 100 μl of mineral oil, the incomplete Freund's adjuvant (IFA, Sigma). The CFA injection produced an area of localized edema and inflammation starting 48 h after injection, with a progressive reduction of the mechanical withdrawal threshold.

Each animal was allowed to develop the arthritis over an 8-9 day period of before testing.

Measurement of Mechanical Allodynia

Rats were placed in individual plastic boxes on a mesh metal floor and allowed to acclimatize for about 30 min. A series of calibrated von Frey hair with logarithmically incremental stiffness (from 2.83 to 5.88×$Log_{10}$ of the bending force, g) were applied to the paw with the up-down method. Each hair was presented perpendicularly against the paw, with sufficient force to cause slight bending, and held approximately 2-3 sec. The filament was recorded when a positive response was noted (paw withdrawn, licking or shaking).

The antiallodynic effect was expressed as % MPE (Maximal Possible Effect) at 2 h post-dosing.

Animal Dosing

The rats were all dosed orally with various doses of an α-aminoamide alone, GBP alone, combined doses of an α-aminoamide and GBP or vehicle. The dosing volume was 2 ml/kg. The dosing materials were all prepared in the vehicle, (distilled water); drug weights were calculated as the free base. For the composition of the invention, the α-aminoamide and GBP (or pregabalin or tiagabine) were both weighted as free base in the chosen ratio of their respective $ED_{50}$ and then dissolved in the appropriate volume to give the final dosing suspension.

Analysis of Antiallodynic Effect

Data are presented as mean of 4/6 animals per group/dose.

Multiple (typically 4) doses of each compound alone were studied for determining the $ED_{50}$. The $ED_{50}$ was defined as the dose producing 50% reversal of mechanical hyperalgesia at 2 h after treatment. An experimental $ED_{50}$ and 95% confidence intervals (CI) were calculated for each compound alone from the linear regressions fitting the experimental data according to the equation y=a+bx.

The different α-aminoamides were then combined with GBP at different ratios in relation to their respective $ED_{50}$ previously calculated (not limiting examples of the ratios are 1:1; 1:3; 1:9 and respectively 1:1, 3:1 and 9:1 ratios) for the evaluation of the synergic effect.

Multiple (typically 4) doses of each selected ratio were then studied orally for evaluating the synergic effect of the combination.

Each rat received only one treatment.

General Method B:

Rat Rotarod Test

The Rotarod test is an established method used as predictive of CNS-related side effects in humans, and in particular motor impairment and ataxia.

Neurological deficit was indicated by the inability of the animal to remain on the rolling apparatus for the entire test time (J. Of the American Pharmaceutical Association, 1957, 46(3).208-209).

Multiple (typically 4-5) doses of each compound alone were studied for determining the $TD_{50}$ i.e. the dose of the tested compound causing 50% of the animals to fall from the roller, calculated by Probit analysis). The different α-aminoamides were then combined with GBP at different ratios in relation to their respective $TD_{50}$ previously calculated (a non limiting example of the ratios is the 1:1 ratio) for the evaluation of the possible synergic effect. Data are presented as mean of 8/10 animals per group/dose.

The test was performed 120 min after drug administration.

Results

By the test "von Frey" for the evaluation of antiallodynic activity, the mean baseline paw withdrawal threshold obtained for the naive control animals was 5.04±0.20 Log [10×force (mg)]; in contrast, the mean rat withdrawal threshold of CFA-treated rats was significantly lower: 3.11±0.11 Log [10×force (mg)]. Vehicle (distilled water) injection had no antihyperalgesic effect in the inflamed paws.

The α-aminoamides given alone and in co-administration with GBP, were NW-1029, NW-1037, NW-1043. Groups were made of 4/6 animals.

All the compounds given alone produced a significant dose related antiallodynic effect, (reversing mechanical hypersensitivity) in inflamed paws.

The $ED_{50}$ estimated for GBP alone, 2 h after single administration was and 12.40 (C.I.: 10.3-14.3) mg/kg (Table 1).

The $ED_{50}$ estimated for NW 1029, NW-1037 and NW-1043 alone, 2 h after single administration, were 0.82 (C.I.: 0.2-4.1), 3.45 (C.I.: 2.3-4.7) and 7.05 (C.I.: 5.8-7.9) mg/kg, respectively (Table 1).

The $ED_{50}$ obtained experimentally ($ED_{50mix}$) from the dose response curve after co-administration of NW-1029, NW-1037 and NW-1043 with GBP at fixed ratios are summarized in Table 1 as well and compared to the additive $ED_{50add}$. The last column of Table 1 reports the calculated amounts of each ingredient of the composition in the experimental $ED_{50mix}$.

The experimental values of $ED_{50mix}$ obtained for the NW-1029/GBP composition of the invention were lower than the calculated additive $ED_{50add}$ for all fixed dose ratios of drugs (see Table 1). Similar data were obtained for the others two compounds NW-1037 and NW-1043 in combination with GBP at the fixed dose ratio of 1:1.

The simultaneous administration of GBP and the active α-aminoamides above defined produces an antinociceptive effect in an animal model of hyperalgesia, which is super-additive.

On the contrary, the effects obtained on the motor functions and ataxia are not super-additive as shown by the results obtained in the Rotarod test (Table 2). In fact, the $TD_{50}$ values obtained with NW-1029 and GBP alone or in the composition of the invention at the 1:1 ratio, in relation to their own $TD_{50}$, are 470, 430 and 480 mg/kg, respectively. Therefore, the data above reported and illustrated confirm that the composition of the invention permits to administer a diminished dose of GBP (or pregabalin or tiagabine) to obtain an effective antinociceptive activity, and to lower its side effects.

TABLE 1

|  | $ED_{50}$ and (CI) p.o. at 2 hours (mg/kg) | | DRUG COMBINATION in the $ED_{50\,mix}$ (mg/kg) | |
|---|---|---|---|---|
|  | $ED_{50\,add}$ (CI) | $ED_{50\,mix}$ (CI) | Test Drug | GBP |
| NW-1029 | 0.82 (0.2-4.1) | | | |
| NW-1037 | 3.45 (2.4-4.8) | | | |
| NW-1043 | 7.05 (5.8-7.9) | | | |
| GBP | 12.40 (10.3-14.5) | | | |
| NW-1029:GBP (1:9) | 11.24 (9.5-12.8) | 5.65 (4.53-6.2) | 0.041 | 5.61 |
| NW-1029:GBP (1:3) | 9.51 (9.0-11.2) | 4.98 (2.5-6.9) | 0.11. | 4.87 |
| NW-1029:GBP (1:1) | 6.62 (4.7-7.3) | 3.12 (1.9-4.2) | 0.19 | 2.92 |
| NW-1029:GBP (3:1) | 3.73 (1.9-4.8) | 1.52 (0.8-1.7) | 0.25 | 1.27 |
| NW-1029:GBP (9:1) | 1.98 (1.7-2.4) | 1.20 (0.7-1.6) | 0.44 | 0.75 |
| NW-1037:GBP (1:1) | 7.92 (6.5-8.7) | 4.03 (2.7-5.8) | 0.87 | 3.17 |
| NW-1043:GBP (1:1) | 9.72 (8.7-10.8) | 7.76 (4.8-8.1) | 2.81 | 4.95 |

$ED_{50\,mix}$ = experimentally estimated $ED_{50}$;
CI = 95% Confidence Intervals;
$ED_{50\,add}$ = theoretically calculated $ED_{50}$ of additivity.

TABLE 2

|  | $TD_{50}$ p.o. at 2 hours (mg/kg) | | DRUG COMBINATION in the $TD_{50\,mix}$ (mg/Kg) | |
|---|---|---|---|---|
|  | $TD_{50\,add}$ (CI) | $TD_{50\,mix}$ (CI) | Test Drug | GBP |
| NW-1029 | 470 | | | |
| GBP | 430 | | | |
| NW-1029:GBP (1:1) | 450 | 480 | 250.6 | 229.4 |

$TD_{50\,mix}$ = experimentally estimated $TD_{50}$;
$TD_{50\,add}$ = theoretically calculated $TD_{50}$ of additivity.

The above reported data show that the composition of the invention permits to administer a diminished dose of GBP in order to obtain an effective antinociceptive activity, while lowering, at the same time, the side effects thereof. The administration of the composition of the invention can be therefore noted to produce an antinociceptive effect in the animal model of hyperalgesia, which is super-additive since the actual $ED_{50mix}$ values, of any of the exemplified composition of the invention, do not fall within the theoretical C.I. ranges.

Following the same experimental protocol above illustrated, the $ED_{50}$ of 4-(4'-fluoro-phenoxy)benzaldehyde semicarbazone, both alone and in combination with gapapentin, in a 1:1 ratio, according to the disclosure of WO 00/61188, was evaluated after oral treatment.

The values of the $ED_{50}$ for said semicarbazone alone (14.5 mg/kg—C.I.: 11.9-15.8) and in combination with gabapentin (13.2 mg/kg—C.I.: 12.1-15.3) were found non-significantly different.

In view of the foregoing, it can be therefore noted that not all the sodium channel blockers, active in a model of chronic pain, as shown by the comparative data above illustrated, are synergic to GBP, adversely to what inadvertently and significantly found out for the α-aminoamides NW-1029, NW-1037 and NW-1043 comprised in the composition of the invention.

The following illustrative examples of pharmaceutical compositions according to the invention are prepared by mixing the ingredients below listed, employing methods usual in the pharmaceutical field.

EXAMPLE 1

α-Aminoamide:GBP Ratio: 1:1

| A capsule contains: | |
|---|---|
| NW-1029 | 13.3 mg |
| GBP | 204.4 mg |
| Talc | 5.7 mg |
| Corn starch | 19.6 mg |
| Microcrystalline cellulose | 52.0 mg |
| Magnesium stearate | 5.0 mg |

EXAMPLE 2

α-Aminoamide: GBP Ratio: 1:3

| A capsule contains: | |
|---|---|
| NW-1029 | 7.7 mg |
| GBP | 341.0 mg |
| Talc | 5.3 mg |
| Corn starch | 20.0 mg |
| Microcrystalline cellulose | 23.0 mg |
| Magnesium stearate | 3.0 mg |

EXAMPLE 3

α-Aminoamide: GBP Ratio: 9:1

| A capsule contains: | |
|---|---|
| NW-1029 | 31.0 mg |
| GBP | 52.5 mg |
| Talc | 3.5 mg |
| Corn starch | 15.0 mg |

-continued

| A capsule contains: | |
|---|---|
| Microcrystalline cellulose | 45.0 mg |
| Magnesium stearate | 3.0 mg |

The invention claimed is:

1. A method for treating chronic inflammatory pain in a mammal in need thereof, comprising administering to the mammal a therapeutically effective dose of a pharmaceutical composition comprising:
gabapentin or pregabalin, or a pharmaceutically acceptable acid addition salt with inorganic or organic acids thereof, and
an α-aminoamide selected from the group consisting of
(S)-(+)-2-[4-(2-fluorobenzyloxy)benzylamino]-propanamide,
(R)-(−)-2-[4-benzyloxybenzylamino]-3-phenyl-N-methylpropanamide, and
(S)-(+)-2-[4-(3-fluorobenzyloxy)-benzylamino]-N-methyl-propanamide,
either as an isolated optically active isomer or as a racemic mixture thereof, or a pharmaceutically acceptable acid addition salt with inorganic or organic acids of the isolated optically active isomer or racemic mixture,
wherein the α-aminoamide and gabapentin or pregabalin or the pharmaceutically acceptable acid addition salts thereof are present in a ratio based on a fraction of their respective $ED_{50}$ values, which ratio ranges from about 1:1 to about 30:1 or from about 1:1 to about 1:30, respectively.

2. A method according to claim 1, wherein the pharmaceutical composition comprises the α-aminoamide and gabapentin or pregabalin, in a ratio based on a fraction of their respective ED50 values, which ratio ranges from about 1:1 to about 9:1 or from about 1:1 to about 1:9, respectively.

3. A method according to claim 1, wherein the pharmaceutical composition comprises the α-aminoamide and gabapentin or pregabalin, in a ratio based on a fraction of their respective ED50 values, which ratio ranges from about 1:1 to about 3:1 or 1:1 to about 1:3, respectively.

4. A method according to claim 1, wherein the pharmaceutical composition comprises gabapentin and the α-aminoamide.

5. A method according to claim 4, wherein gabapentin and the α-aminoamide are in a ratio, based on a fraction of their respective $ED_{50}$ values, of from about 1:1 to about 9:1 or from about 1:1 to about 1:9.

6. A method according to claim 4, wherein gabapentin and the α-aminoamide are in a ratio, based on a fraction of their respective $ED_{50}$ values, of from about 1:1 to about 3:1 or from about 1:1 to about 1:3.

7. A method according to claim 1 or claim 4, wherein the α-aminoamide is (S)-(+)-2-[4-(2-fluorobenzyloxy)benzylamino]propanamide or a pharmaceutically acceptable acid addition salt thereof.

8. A method according to claim 1, wherein the mammal in need of the said treatment is administered a dose of the pharmaceutical composition which ranges from about 0.05 to about 50 mg/day per kg of body weight.

* * * * *